United States Patent [19]

Norton

[11] 4,091,010

[45] May 23, 1978

[54] PROCESS FOR THE PREPARATION OF CYANOHYDRIN ESTERS

[75] Inventor: Richard V. Norton, Wilmington, Del.

[73] Assignee: Suntech, Inc., Wayne, Pa.

[21] Appl. No.: 736,667

[22] Filed: Oct. 28, 1976

[51] Int. Cl.$^2$ .................. C07C 120/00; C07C 121/66
[52] U.S. Cl. ........................... 260/465 D; 260/465 C
[58] Field of Search ........... 260/465 C, 465 D, 465 F, 260/599

[56] References Cited

U.S. PATENT DOCUMENTS

| | | | |
|---|---|---|---|
| 3,787,477 | 1/1974 | Matthews | 260/465 F |
| 3,931,330 | 1/1976 | Aprahamian | 260/599 |
| 3,987,079 | 10/1976 | Ray et al. | 260/465 F |

Primary Examiner—Dolph H. Torrence
Attorney, Agent, or Firm—J. Edward Hess; Donald R. Johnson; Paul Lipsitz

[57] ABSTRACT

In the liquid phase catalytic oxidation of alkylsubstituted aromatic compounds to the corresponding aldehyde and alcohols the improvement of modifying the reaction to yield the corresponding cyanohydrin ester, which comprises carrying out said oxidation in the presence of HCN or an alkali metal cyanide and an anhydride of the ester moiety.

4 Claims, No Drawings

PROCESS FOR THE PREPARATION OF CYANOHYDRIN ESTERS

Cyanohydrin derivatives of aromatic compounds are of particular value as intermediates to pyrethrin insecticides. For example, the extremely active insecticide known as decamethrin (NRDC-161) has the structure

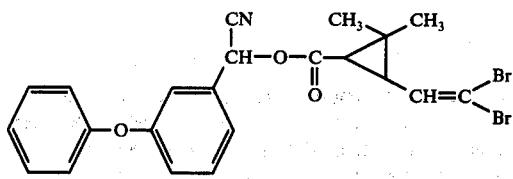

and may be derived from the corresponding cyanohydrin and chrysanthemummonocarboxylic acid (Ger. Offen. No. 2,231,312). To obtain the cyanohydrin it is necessary to react HCN with the appropriate aldehyde, which in turn, may be prepared by liquid phase oxidation of the appropriate alkyl substitute aromatic compound or hydrolysis of a dichloromethyl substituent. In this oxidation, both aldehyde, alcohol and corresponding acid are obtained, thus requiring separation of the derived aldehyde in relatively low yield and resulting in a very inefficient overall process.

It has now been found that the desired cyanohydrin, in the form of its ester, can be obtained directly from the alkyl substituted aromatic compound used for the oxidation step and this is accomplished by carrying out the oxidation reaction in the presence of HCN or an alkali metal cyanide and an anhydride of the ester moiety desired.

The liquid phase oxidation of alkyl substituted aromatic compounds is well known (e.g. U.S. Pat. No. 3,931,330) being generally carried out at about 100° to about 140° using oxygen (air) as an oxidant and in the presence of a catalytic amount any one of numerous available catalysts; e.g. a transition metal in the form of an organic acid salt and preferably a cobalt salt such as cobalt acetate. (U.S. Pat. No. 3,649,675), manganic acetate (Fr. No. 2,030,543), cobaltous 2-ethyl hexanoate and the like. The reaction may be carried out neat or with solvents such as acetic acid and acetic anhydride. The alkyl substituted aromatic compound may be selected from any of the wide variety of compounds amenable to the oxidation and will include, preferably, compounds of structure $R_1$-Ar-$(R_2)_n$ where Ar is an aromatic group, preferably containing from 6 to 12 carbon atoms (i.e. of the benzene and naphthalene series), $R_1$ is a lower alkyl group (i.e., of one to four carbon atoms), $R_2$ is an inert substituent on the aromatic ring, and n is zero or an integer of from 1 to 4. It will be understood that $R_2$ may include any substituent inert to the reaction and will preferably be alkoxy, aryloxy (e.g. phenoxy), halo and cyano.

As indicated above, in carrying out the process of the invention, the liquid phase oxidation will be conducted in the usual manner with the inclusion in the reaction mass of HCN or an alkali metal cyanide and an anhydride of the ester moiety that is desired. Of the alkali metal cyanides, KCN and NaCN will be preferred. The preferred anhydride will be acetic anhydride as this will yield the acetate and although others can be used there would be little reason to use the more expensive propionic acid anhydride and higher anhydrides. Special conditions when usng HCN involve the recognition of the hazards and using pressure transfer systems to enhance safety.

The amount of HCN or alkali metal cyanide which will be used in the reaction mass needs to be at least about one mole per mole of the alkyl substituted aromatic compound converted by the oxidation and preferably 1 to 1.5 moles per mole. Likewise the amount of anhydride will be in stoichiometric excess of the oxidation reaction, but no more than about a 5 to 10 molar excess will be used (based on an assumed maximum of 10% oxidation conversion of charged hydrocarbon) because of the adverse effect it may have on some catalysts in promoting benzylidene diacetate as a by-product.

In place of using acetic anhydride, it is equally effective to carry out the oxidation in glacial acetic acid. Upon completion of the reaction acetic anhydride is simply added to efffect dehydration and give the acetate ester of the cyanohydrin.

After the reaction is completed the product cyanohydrin is readily separated by distillation and the product is generally of sufficient purity to be ready for use.

The cyanohydrin ester product obtained by the process of the invention is of particular value for making pyrethrin type insecticides, such as Decamethrin. In particular, the cyanohydrin ester may be transesterfied with an appropriate acid ester to yield the desired product. Thus, to make a pyrethroid, the cyanohydrin acetate obtained by the process of this invention from m-phenoxy toluene is transesterfied with the appropriate methyl ester of chrysanthemumic acid:

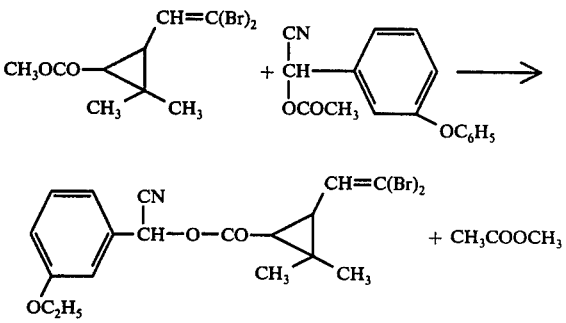

The above reaction is carried out in an inert hydrocarbon in the presence of a catalyst, preferably a weak acid in exchange resin that can be easily separated from the system (e.g. filtration). The product is recovered from the solvent or the solvent system may be used directly to impregnate the carrier of the insecticide.

In order to further illustrate the process of the invention the following examples are given:

EXAMPLE 1

A stirred 2-liter autoclave is charged with toluene (400g), cobaltous 2-ethyl hexanoate (2g), acetic anhydride (50g) and potassium cyanide (25g) in that order in the confines of a well ventilated hood. The autoclave is sealed, flushed with $N_2$ and heated to 150° whereupon the $N_2$ pressure of 176 psig is increased to 220 psig with oxygen. The oxygen pressure is maintained at 45 psig during the reaction and at completion of the reaction the product is isolated by distillation. At 1.5% conversion of the toluene there is a 25% yield of benzyl acetate and 72% yield of 2-cyanobenzyl acetate based on the toluene converted.

EXAMPLE 2

A stirred 2-liter autoclave was charged with toluene (400g), cobalt acetate (0.5g), acetic anhydride (100g) and potassium cyanide (25g)$_o$. The system is oxidized at 180° C for 3 hours using a 90/10 nitrogen/oxygen mixture. VPC analysis of the oxidate shows about 18% toluene conversion with a 30% yield of cyanohydrin acetate based on toluene oxidized.

EXAMPLE 3

A stirred 2-liter autoclave is charged with toluene (400g) cobaltous 2-ethylhexanoate (2.5g) and potassium cyanide (25g), flushed with nitrogen and sealed. Acetic acid (200g) is then pressured into the reactor and oxidation is carried out at 150° using a 90/10 mixture of $N_2/O_2$. The reaction mixture is cooled to room temperature and carefully opened in a well ventilated hood, whereupon acetic anhydride (20000) is added and the oxidant refluxed for 1 hour. VPC analysis indicates a 10% conversion of toluene and a 30% yield of 2-cyanobenzylacetate based on the toluene oxidized.

EXAMPLE 4

In the manner of Example 1 the reaction of 150g of m-phenoxy toluene, 2g. cobaltous acetate, 50g. of acetic anhydride and 15g. of KCN is carried out in a 1 liter Parr reactor at 180° C. using a 90/10 mixture of $N_2/O_2$. Pure oxygen is added to the reactor over a period of 1.5 hours as the pressure decreases. A 20% conversion of the m-phenoxy toluene to the corresponding cyanohyrin acetate is obtained to give a 30% yield of product based on conversion.

The invention claimed is:

1. The process of making a cyanohydrin ester of an alkyl-substituted aromatic acid which comprises the liquid phase oxidation of an alkyl aromatic compound of the structure $$R_1\text{-}A_2\text{-}(R_2)_n$$

where $A_2$ is an aromatic group of 6 to 12 carbon atoms, $R_1$ is a lower alkyl group, $R_1$ is an inert substituent on the aromatic ring and n is zero or an integer of from 1 to 4 usng air as oxidant and in the presence of a catalytic amount of a transition metal catalyst and in the presence of HCN or an alkali metal cyanide and an anhydride of the ester desired, said HCN or alkali metal cyanide being present in an amount of at least about one mole per mole of the alkyl substituted aromatic compound oxidized and the amount of said anhydride being in stoichiometric excess of the oxidation reaction up to a 10 molar excess.

2. The process of claim 1 where the anhydride is acetic anhydride.

3. The process of claim 2 where the aromatic compound is toluene.

4. The process of claim 2 when the aromatic compound is m-phenoxy toluene.

* * * * *